United States Patent [19]

Morton

[11] Patent Number: 4,504,408

[45] Date of Patent: Mar. 12, 1985

[54] FLUORESCENT VAPOR FUMES FOR USE WITH A SELF-CONTAINED FINGERPRINTING KIT

[76] Inventor: William P. Morton, 11260 Missouri Ave., Los Angeles, Calif. 90025

[21] Appl. No.: 535,023

[22] Filed: Sep. 23, 1983

[51] Int. Cl.³ .............................................. C09K 11/06
[52] U.S. Cl. ................................. 252/301.16; 106/19; 106/21; 106/22; 118/31.5; 118/719; 118/733; 252/372; 252/374; 427/1; 427/68; 427/145; 427/157; 427/255.4; 427/345; 283/69
[58] Field of Search ........................... 118/31.5; 427/1; 252/301.16

[56] References Cited

U.S. PATENT DOCUMENTS

| | | | |
|---|---|---|---|
| 2,066,535 | 1/1937 | Lucas | 427/1 |
| 2,938,292 | 5/1960 | Jaskowsky | 118/31.5 |
| 4,145,300 | 3/1979 | Hendriks | 252/62.54 |
| 4,176,205 | 11/1979 | Molina | 427/1 |
| 4,258,073 | 3/1981 | Payne | 427/1 |
| 4,258,644 | 3/1981 | Goettert | 118/31.5 |
| 4,260,645 | 4/1981 | Kerr et al. | 427/1 |
| 4,297,383 | 10/1981 | Bourdon | 427/1 |
| 4,379,178 | 4/1983 | Meadows | 427/1 |
| 4,381,159 | 4/1983 | Payne | 118/31.5 |
| 4,407,842 | 10/1983 | Shepard | 427/1 |

Primary Examiner—Arthur P. Demers
Attorney, Agent, or Firm—W. Edward Johansen

[57] ABSTRACT

The present invention is a vapor phase activator pad which produces fluorescent vapor fumes for use in a self-contained fingerprinting kit. The vapor phase activator pad is placed into an enclosed area order to fume an object in the area suspected of containing latent fingerprints. The vapor phase activator pad includes a fluorescent dye impregnated gauze pad and a composition. The composition consists of specified chlorinated organic solvents. The gauze pad is chemically treated with the composition so that when a quantity of alkyl-cyanoacrylate is placed onto the vapor phase activator pad. The vapor phase activator pad generates fluorescent vapors of the chemical cyanoacrylate wherein the latent fingerprints become exposed when an ultraviolet light source is shined on the object suspected of containing the latent fingerprints.

6 Claims, 4 Drawing Figures

FLUORESCENT VAPOR FUMES FOR USE WITH A SELF-CONTAINED FINGERPRINTING KIT

BACKGROUND OF THE INVENTION

1. Field of the Invention

The present invention relates to a system for fuming an object suspected of containing latent fingerprints thereon with vapors of the chemical cyanoacrylate and more particularly to a gauze pad which is treated with a fluorescent dyes and a composition which includes chlorinated organic solvents and which functions as a base for activating an alkyl-cyanoacrylate fuming acton in order to generate rapid and prolonged fuming with the fluorescent vapors.

2. Description of the Prior Art

U.S. Pat. No. 4,297,383, entitled Apparatus and Method for Obtaining Fingerprints, issued to Louis P. Bourdon on Oct. 27, 1981, teaches an apparatus and method for developing latent fingerprints on an object. The apparatus includes a first chamber which contains the object and which closes in order to seal the first chamber air-tight and form a vapor tank and a second chamber which contains a chemical pool and vapors thereof. The apparatus also includes a pump system which pumps vapors from the second chamber into the vapor tank. The method includes the step of pumping the vapors into the vapor tank in order to fume the object with the vapors of the chemical cyanoacrylate and to develop the latent fingerprints on the object being tested inside the vapor tank. U.S. Pat. No. 3,546,003 teaches a similar apparatus and method for obtaining latent fingerprints.

U.S. Pat. No. 4,260,645, entitled Latent Fingerprint Detection, issued to F. Michael Kerr and Alan D. Westland on April 7, 1981, teaches a method of detecting and visualizing a latent fingerprint which includes the step of applying a solution to a suspected locale. The solution includes a volatile organic solvent and selected salts soluble in the volatile organic solvent. The salts include silver perchlorate and silver trifluoroacetate. The nonaqueous solution is preferrably applied as a spray and minimizes smudging, "running", warping, and other damage to water-sensitive materials such as inks, dyes and/on cellulosis substrates.

U.S. Pat. No. 4,258,073, entitled Taking of Finger Prints, issued to John M. Payne on Mar. 24, 1981, teaches a method of revealing a fingerprint which includes the steps of charging a surface bearing the fingerprint to a high electric potential and applying a finely divided carbon to the charged surface in order to form a pattern thereon which corresponds to the fingerprint. The method of revealing a fingerprint also includes the steps of either dusting or spraying the finely divided carbon onto the charged surface and applying a transparent protective layer in order to fix the pattern of finely divided carbon in position. Alternatively the finely divided carbon may be in suspension in a dielectric liquid into which the charged surface is introduced.

U.S. Pat. No. 4,381,159, entitled Magnetic Fingerprint Dusting Brush, issued to John M. Payne on April 26, 1983, teaches a magnetic fingerprint dusting brush which includes a handle which incorporates a magnetic portion that projects at one end thereof and a non-magnetic shroud which is assembled with the handle closely to shroud the projecting mnagnetic portion. The shroud includes an inner blind sleeve for closely shrouding the projecting magnetic portion and an outer sleeve to which a cover is detachably secured. The inner blind sleeve has a first portion of greater cross-section for assembly with the handle and a coaxial second portion of lesser cross-section which is connected to the first portion through a shoulder for closely shrouding the projecting magnetic portion. The magnetic fingerprint dusting brush also includes a cover which is detachably securable to the handle and shroud assembly to form in its secured position an enclosed powder reservoir around the shrouded magnetic portion of the handle. The shroud and the cover assembly constitute a powder cartridge with the handle. The powder reservoir contains a mixture of ferrous and dusting powder.

U.S. Pat. No. 4,379,178, entitled Fingerprinting System, issued to Louis B. Meadows and Arthur S. Diamond on April 5, 1983, teaches a method for forming fingerprint images which includes the steps of prewetting and cleaning the portion of a finger with a cloth impregnated with a detergent solution and applying the distal portion of a finger to a porous pad impregnatred with a solution of marking compound. The method for forming fingerprint images also includes the steps of applying the distal portion of the finger to square of a fingerprint card impregnated with an aqueous solution of a polyhydroxy developer, such as a solution of 8-hydroxy-quinoline and propyl gallate containing a high molecular weight dibasic acid, such as azelaic acid and, when the fingerprint image immediately develops, removing traces of the images with a cloth impregnated with a cleaning solution.

U.S. Pat. No. 4,258,644, entitled Depositing Latent Fingerprints and Development Thereof, issued to Edward J. Goettert and George V. D. Tiers on Mar. 31, 1981, teaches a method of depositing and developing a latent fingerprint which includes the steps of making a composition which includes a trimeric aliphatic acid of at least 30 carbon atoms which is substantive to paper fibers, substantially non-volatile, non-hardneing, non-toxic and non-hydroscopic and using the composition to apply the fingerprint, which has a latency of several weeks, to a paper substrate. The method of depositing and developing a latent fingerprint also includes the steps of dusting the latent fingerprints in the conventional manner with a suitable toner particles, such as magnetic particles in an oleophilic matrix and developing the latent fingerprint

SUMMARY OF THE INVENTION

In view of the foregoing factors and conditions which are characteristic of the prior art it is the primary object of the present invention to provide a system for fuming an object suspected of containing latent fingerprints thereon with fluorescent vapors of the chemical cyanoacrylate.

It is another object of the present invention to provide a a gauze pad which is treated with a fluorescent dye and a composition which includes chlorinated organic solvents and which functions as a base for activating an alkyl-cyanoacrylate fuming acton in order to generate rapid and prolonged fuming with the fluorescent vapors.

It is still another object of the present invention to provide a fluorescent dye impregnated gauze pad which is treated with a first chemical and second chemical and which generates fluorescent vapors of the chemical cyanoacrylate for rapid and prolonged fuming for use in a system for fuming an object suspected of containing latent fingerprints.

In accordance with an embodiment of the present invention vapor phase activator pad which produces fluorescent vapor fumes for use in a self-contained fingerprinting kit is described. The vapor phase activator pad is placed into an enclosed area order to fume an object in the area suspected of containing latent fingerprints. The vapor phase activator pad includes a fluorescent dye impregnated gauze pad and a composition. The composition consists of specified chlorinated organic solvents. The gauze pad is chemically treated with the composition so that when a quantity of alkyl-cyanoacrylate is placed onto the vapor phase activator pad. The vapor phase activator pad generates fluorescent vapors of the chemical cyanoacrylate wherein the latent fingerprints become exposed when an ultraviolet light source is shined on the object suspected of containing the latent fingerprints.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
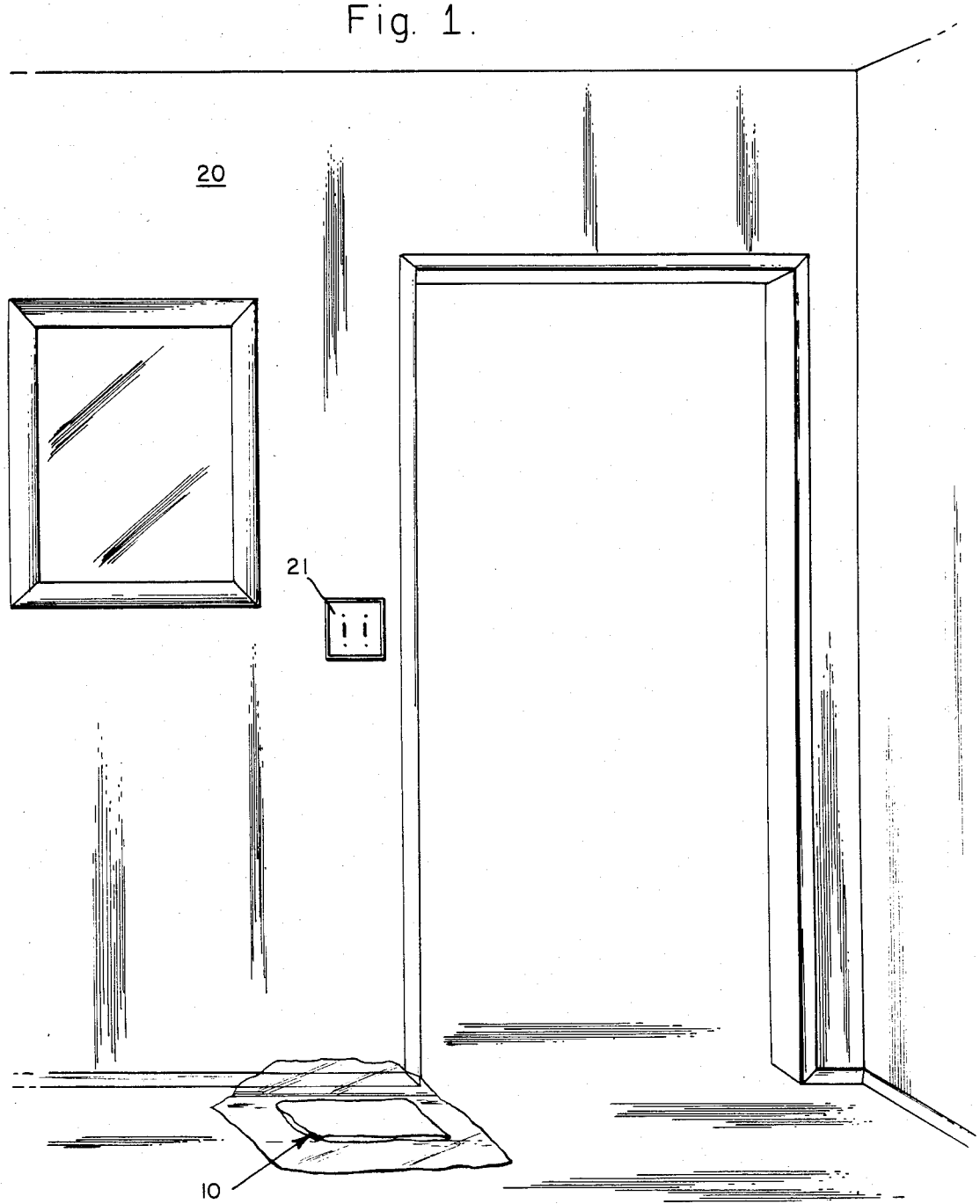
FIG. 1 is a schematic drawing of a wall with a light switch which is disposed adjacent to a door frame and which is suspected of containing latent fingerprints and a vapor phase activator pad which is treated with a fluorescent dyes and a composition which includes chlorinated organic solvents in accordance with the principles of the present invention.
Figure 2:
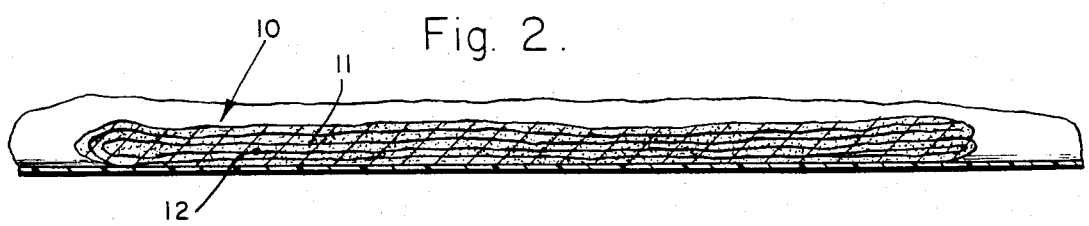
FIG. 2 is an elevational view in cross-section of the vapor phase activator pad of FIG. 1.

In order to best understand the present invention it is necessary to refer to the following description of its preferred embodiment in conjunction with the accompanying drawing. Referring to FIG. 1 in conjunction with FIG. 2 a vapor phase activator pad 10 which includes a gauze pad 11 impregnated with a fluorescent dye, such a Rhodamine B, and treated with a composition 12 which consists of specified chlorinated organic solvents. The composition 12 includes a first component and a second component.

The first component may be a mixture of two selective chemicals, chlorothane in the range of 1 to 96 percent and stabilized with methanol in the range of 1 to 10 percent. The second component may be a mixture of four selective chemicals, nitroethane and nitromethane in the range of 1 to 5 percent and stabilized with toluene in the range of 1 to 4 percent. The second component may also include an activator which is diethylenetriamine in the range of 1 to 9 percent. The composition provides a controlled oxidative vaporization of the quantities of alkyl-cyanoacrylate.

The first component may be a mixture of two selective chemicals, chlorothane in the range of 1 to 96 percent and stabilized with methanol in the range of 1 to 10 percent. The second component may be a mixture of three selective chemicals, nitroethane in the range of 1 to 5 percent and stabilized with toluene in the range of 1 to 4 percent. The second component may also include an activator which is diethylenetriamine in the range of 1 to 9 percent wherein said composition provides a controlled oxidative vaporization of said quantity of alkyl-cyanoacrylate.

The first component may be a mixture of two selective chemicals, chlorothane in the range of 1 to 96 percent and stabilized with methanol in the range of 1 to 10 percent. The second component may be a mixture of three selective chemicals, nitromethane in the range of 1 to 5 percent and stabilized with toluene in the range of 1 to 4 percent. The second component may also include an activator which is diethylenetriamine in the range of 1 to 9 percent wherein said composition provides a controlled oxidative vaporization of said quantity of alkyl-cyanoacrylate.

Still referring to FIG. 1 a wall 20 has a light switch 21 which is disposed adjacent to a door frame. It is suspected that the light switch 21 contains latent fingerprints. The vapor phase activator pad 10 is placed into an enclosed area adjacent the wall 20 and beneath the light switch 21 in order to fume an object in the area suspected of containing latent fingerprints.

Figure 3:
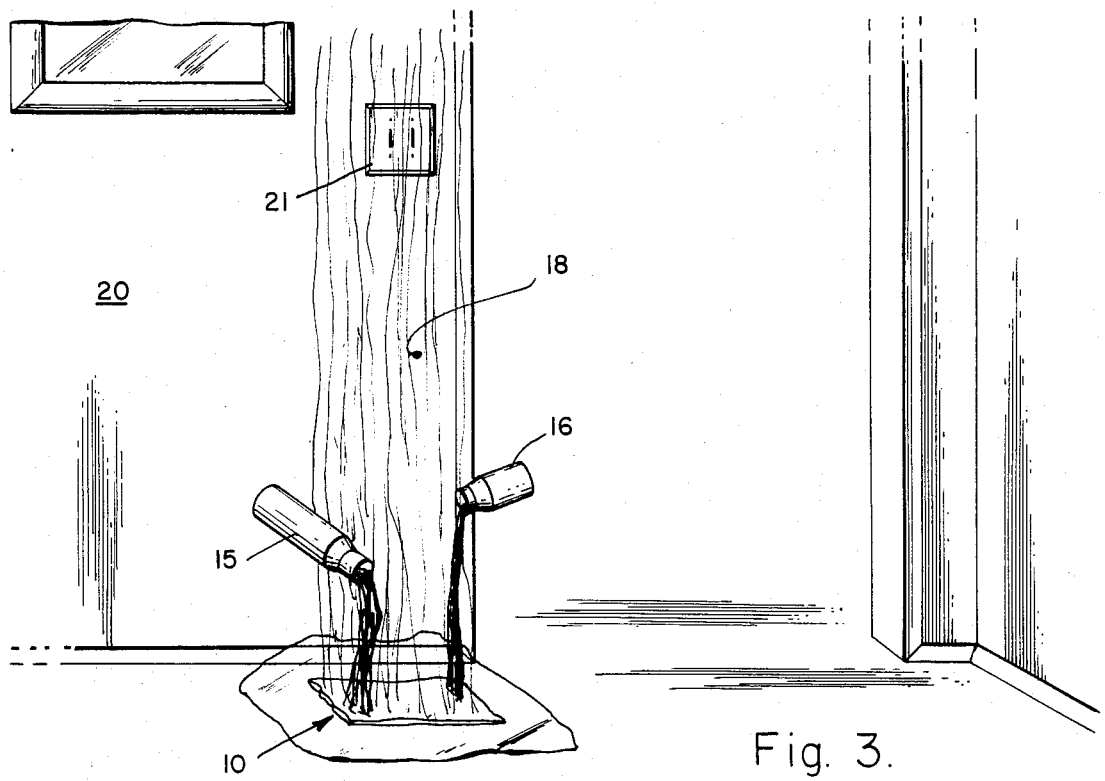
FIG. 3 is a schematic of part of the wall including the light switch and the vapor phase activator pad of FIG. 1 wherein an alkyl-cyanoacrylate illustrating solution is poured onto the gauze pad which functions as a base for activating an alkyl-cyanoacrylate fuming acton in order to generate rapid and prolonged fuming of the light switch which is suspected of containing latent fingerprints with the fluorescent vapors.

Referring to FIG. 3 the fluorescent dye impregnated gauze pad 11 has been chemically treated with the composition 12 so that when quantities of alkyl-cyanoacrylate from a first container 15 and a second container 16 are placed onto the vapor phase activator pad 10, the vapor phase activator pad 10 generates fluorescent vapors 18 of the chemical cyanoacrylate.

In another embodiment of the present invention a vapor phase activator pad and treated with a composition which consists of specified chlorinated organic solvents. The gauze pad has been chemically treated with the composition so that when a mixture of a fluorescent dye, such as Hostasol yellow 8G, which American Hoechst Corporation manufactures, and quantities of alkyl-cyanoacrylate from a first container and a second container are placed onto the vapor phase activator pad, the vapor phase activator pad generates fluorescent vapors of the chemical cyanoacrylate.

Figure 4:
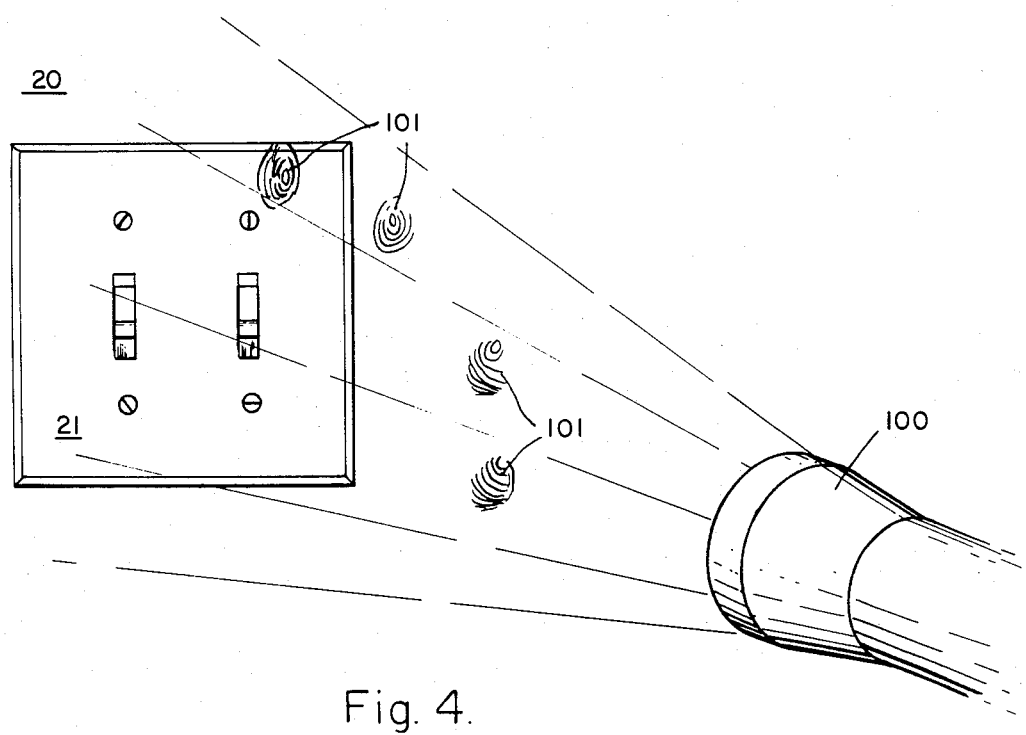
FIG. 4 is a schematic of the light switch which is suspected of containing latent fingerprints, after the light switch has been fumed with fluorescent vapors and when an ultraviolet light source is shined on the light switch in order to expose latent fingerprints, if any, on the light switch.

Referring to FIG. 4 an ultraviolet source exposes latent fingerprints 101 when the ultraviolet light source 100 is shined on the object containing the latent fingerprints 101.

From the foregoing it can be seen that a vapor phase activator pad for fuming an object suspected of containing latent fingerprints thereon with fluorescent vapors of the chemical cyanoacrylate has been described.

Accordingly it is intended that the foregoing disclosure and showing made in the drawing shall be considered only as an illustration of the principles of the present invention.

What is claimed is:

1. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:
   a. a fluorescent dye impregnated gauze pad;
   b. a composition which consists of a first component which is a mixture of two selective chemicals, chlorothane in the range of 1 to 96 percent and stabilized with methanol in the range of 1 to 10 percent and a second component which is a mixture of four selective chemicals, nitroethane and nitromethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate whereby said fluorescent dye impregated gauze pad is chemically treated with said composition so that when a quantity of alkyl-cyanoacrylate is placed onto said vapor phase activator pad, said vapor phase activator pad generates fluorescent vapors of the chemical cyanoacrylate wherein said latent fingerprints become exposed when an ultraviolet light source is shined on said object containing said latent fingerprints.

2. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:
   a. a fluorescent dye impregnated gauze pad;
   b. a composition which consists of a first component which is a mixture of two selective chemicals, chlorothane in the range of 1 to 96 percent and stabilized with methanol in the range of 1 to 10 percent and a second component which is a mixture of three selective chemicals, nitroethane in the range of 1 to 5 percent and stabilized with toluene in the range of 1 to 10 percent, said second component also includes an activator which is diethylenetriamine in the range of 1 to 9 percent wherein said composition provides a controlled oxidative vaporization of said quantity of alkyl-cyanoacrylate wherein said composition provides a controlled oxidative vaporization of said quantity of alkyl-cyanoacrylate whereby said fluorescent dye impregnated gauze pad is chemically treated with said composition so that when a quantity of alkyl-cyanoacrylate is placed onto said vapor phase activator pad, said vapor phase activator pad generates fluorescent vapors of the chemical cyanoacrylate wherein said latent fingerprints become exposed when an ultraviolet light source is shined on said object containing said latent fingerprints.

3. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:
   a. a fluorescent dye impregnated gauze pad;
   b. a composition which consists of a first component which is a mixture of two selective chemicals, chlorothane in the range of 1 to 96 percent and stabilized with methanol in the range of 1 to 10 percent and a second component which is a mixture of three selective chemicals, nitromethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate wherein said composition provides a controlled oxidative vaporization of said quantity of alkyl-cyanoacrylate whereby said fluorescent dye impregnated gauze pad is chemically treated with said composition so that when a quantity of alkyl-cyanoacrylate is placed onto said vapor phase activator pad, said vapor phase activator pad generates fluorescent vapors of the chemical cyanoacrylate wherein said latent fingerprints become exposed when an ultraviolet light source is shined on said object containing said latent fingerprints.

4. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:
   a. a gauze pad;
   b. a mixture of alkyl-cyanoacrylate and a fluorescent dye;
   c. a composition which consists of a first component which is a mixture of two selective chemicals, chlorothane in the range of 1 to 96 percent and stabilized with methanol in the range of 1 to 10 percent and a second component which is a mixture of four selective chemicals, nitroethane and nitromethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate whereby said gauze pad is chemically treated with said composition so that when said mixture of alkyl-cyanoacrylate and said fluorescent dye is placed onto said vapor phase activator pad, said vapor phase activator pad generates fluorescent vapors of the chemical cyanoacrylate wherein said latent fingerprints become exposed when an ultraviolet light source is shined on object suspected of containing said latent fingerprints.

5. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:
   a. a gauze pad;
   b. a mixture of alkyl-cyanoacrylate and a fluorescent dye;
   c. a composition which consists of a first component which is a mixture of two selective chemicals, chlorothane in the range of 1 to 96 percent and stabilized with methanol in the range of 1 to 10 percent and a second component which is a mixture of three selective chemicals, nitroethane in the range of 1 to 5 percent and stabilized with toluene in the range of 1 to 10 percent, said second component also includes an activator which is diethylenetriamine in the range of 1 to 9 percent wherein said composition provides a controlled oxidative vaporization of said quantity of alkyl-cyanoacrylate wherein said composition provides a controlled oxidative vaporization of said quantity of alkyl-cyanoacrylate whereby said gauze pad is chemically treated with said composition so that when said mixture of alkyl-cyanoacrylate and said fluorescent dye is placed onto said vapor phase activator pad, said vapor phase activator pad generates fluorescent vapors of the chemical cyanoacrylate wherein said latent fingerprints become exposed when an ultraviolet light source is shined on object suspected of containing said latent fingerprints.

6. A vapor phase activator pad which produces fluorescent vapor fumes for use in a self-contained fingerprinting kit wherein said vapor phase activator pad is placed into an enclosed area order to fume an object in the area suspected of containing latent fingerprints, said vapor phase activator pad comprising:

a. a gauze pad;
   b. a mixture of alkyl-cyanoacrylate and a fluorescent dye;
   c. a composition which consists of a first component which is a mixture of two selective chemicals, chlorothane in the range of 1 to 96 percent and stabilized with methanol in the range of 1 to 10 percent and a second component which is a mixture of three selective chemicals, nitromethane in the range of 1 to 5 percent and stabilized with toluene in the range of 1 to 4 percent, said second component also includes an activator which is diethylenetriamine in the range of 1 to 9 percent wherein said composition provides a controlled oxidative vaporization of said quantity of alkyl-cyanoacrylate wherein said composition provides a controlled oxidative vaporization of said quantity of alkyl-cyanoacrylate whereby said gauze pad is chemically treated with said composition so that when said mixture of alkyl-cyanoacrylate and said fluorescent dye is placed onto said vapor phase activator pad, said vapor phase activator pad generates fluorescent vapors of the chemical cyanoacrylate wherein said latent fingerprints become exposed when an ultraviolet light source is shined on object suspected of containing said latent fingerprints.

* * * * *